(12) United States Patent
Pham

(10) Patent No.: US 8,747,852 B1
(45) Date of Patent: Jun. 10, 2014

(54) METHODS OF TREATING PTERYGIUM

(71) Applicant: Randal Tanh Hoang Pham, San Jose, CA (US)

(72) Inventor: Randal Tanh Hoang Pham, San Jose, CA (US)

( * ) Notice: Subject to any disclaimer, the term of this patent is extended or adjusted under 35 U.S.C. 154(b) by 0 days.

(21) Appl. No.: 13/830,819

(22) Filed: Mar. 14, 2013

Related U.S. Application Data

(60) Provisional application No. 61/746,778, filed on Dec. 28, 2012.

(51) Int. Cl.
*A61K 39/395* (2006.01)
*A61P 29/00* (2006.01)

(52) U.S. Cl.
USPC .................. 424/133.1; 424/130.1; 424/145.1; 514/12.2; 514/13.3

(58) Field of Classification Search
None
See application file for complete search history.

(56) References Cited

FOREIGN PATENT DOCUMENTS

WO    WO2007/038453    4/2007

OTHER PUBLICATIONS

"Safety Study of Avastin Used as Adjunctive Therapy in Pterygium Surgery" by the University of Texas Health Science Center, Houston; Clinical Trials.gov; http://clinicaltrials.gov/ct2/show/NCT01115517; ; last accessed Aug. 13, 2012.
Ferrara et al. "Bevacizumab (Avastin), a humanized anti-VEGF monoclonal antibody for cancer therapy" Biochemical and Biophysical Research Communications 333 (2005) 328-335.
Tirgan, Michael H., M.D. "Therapeutic Study of Bevacizumab Injection Directly Inside the Keloid Tissue" Clnical Trials. gov; http://clinicaltrials.gov/ct2/show/NCT01408953; last accessed Aug. 13, 2012.
Fallah et al. "Efficacy of Topical Bevacizumab for Inhibiting Growth of Impending Recurrent Pterygium" Current Eye Research, 35(1), 17-22,2010.
Bahar et al. "Subconjunctival Bevacizumab Injection for Corneal Neovascularization in Recurrent Pterygium" Current Eye Research, 33:23-28, 2008.
Hosseini et al. "Bevacizumab (Avastin) as a potential novel adjunct in the management of pterygia" Medical Hypotheses (2007) 69,925-927.
Besharati et al. "Subconjunctival Bevacizumab Injection in Treatment of Pterygium" Acta Medica Iranica 2011; 49(3): 179-183.
Sinha et al. "Anti-vascular endothelial growth factor in ophthalmology" Indian J Ophthalmol. Jul.-Aug. 2009; 57(4): 330-335.
Enkvetchakul et al. "A randomized controlled trial of intralesional bevacizumab injection on primary pterygium: preliminary results." Cornea. Nov. 2011;30(11):1213-8.
Pham, R. "Successful Prevention of Symblepharon Formation and Pterygium Regrowth with Bevacizumab" Abstract; Presented at the American Society of Ophthalmic Plastic and Reconstructive Surgery Spring Meeting in Tucson, Arizona (May 2012).
Young, M. "Study finds new possible treatment for pterygium" EyeWorld (online publication); published online Jul. 2011; http://www.eyeworld.org/printarticle.php?id=5931; Last Accessed Mar. 11, 2013.
Copenheaver, Blaine R., authorized officer, International Search Report and Written Opinion for PCT application No. PCT/US2013/077853, mailed Mar. 21, 2014, 9 pages.

*Primary Examiner* — Christine J Saoud
*Assistant Examiner* — Jon M Lockard
(74) *Attorney, Agent, or Firm* — Fish & Richardson P.C.

(57) ABSTRACT

Methods for treating pterygium recurrence following pterygiectomy, and for treating keloid recurrence, following surgical removal of the keloid, are disclosed. The methods include administering an anti-VEGF agent (e.g., antibody (e.g., bevacizumab) or small molecule inhibitor of VEGF signaling), or a combination therapy that includes co-administering an anti-VEGF agent, with an anti-inflammatory steroid and/or a non-steroidal anti-inflammatory drug (NSAID) to a subject.

30 Claims, 5 Drawing Sheets

METHODS OF TREATING PTERYGIUM

RELATED APPLICATIONS

The present application claims the benefit of U.S. Provisional Patent Application Ser. No. 61/746,778, filed Dec. 28, 2012, which is herein incorporated by reference in its entirety.

TECHNICAL FIELD

The present disclosure relates to methods of treating eye and skin conditions, in particular, methods for treating pterygium and keloid, including treating recurrence of these conditions following surgery.

BACKGROUND

Pterygium is a fibrovascular conjunctiva proliferation of the supra-ocular surface with extension to the cornea. Surgery is the accepted method for primary treatment of pterygium; however, one of the major limitations of surgical management of pterygium is the high recurrence rate. The growth factor, vascular endothelial growth factor (VEGF), has been shown to be highly expressed in pterygium and in the growing blood vessels that are associated with pterygium recurrence.

Bevacizumab (Avastin®) is a 149-Kd full length humanized anti-vascular endothelial growth factor (anti-VEGF) antibody that has been used off-label as a therapy for ocular neovascular diseases, such as age-related macular degeneration. Others have also found that subconjunctival administration of bevacizumab provided temporary treatment of recurrent pterygium.

Keloid is chronic skin conditions that results in formation of tumor-like growths on the skin. Despite its benign nature, keloid can cause severe aesthetic and, in some cases, functional problems which negatively impacts a person's quality of life. Like pterygia, keloid tissue expresses excessive amounts of VEGF, which may play a role in the formation and evolution of keloid.

SUMMARY OF THE INVENTION

In certain aspects, the present disclosure provides a method for treating pterygium recurrence comprising administering to an affected eye of a subject in need of such treatment (1) an anti-VEGF agent; and one or both of (2) an anti-inflammatory steroid and (3) a non-steroidal anti-inflammatory drug (NSAID). In certain aspects, the method comprises administering (1) an anti-VEGF agent and (2) an anti-inflammatory steroid to the affected eye of the subject. In certain aspects, the treatment comprises administering (1) an anti-VEGF agent and (3) an NSAID to the affected eye of the subject. In some aspects, the treatment comprises administering (1) an anti-VEGF agent, (2) an anti-inflammatory steroid and (3) an NSAID to the affected eye of the subject. In certain aspects, the anti-VEGF agent is an antibody or small molecule inhibitor of VEGF signaling. In other aspects, the anti-VEGF agent is an antibody. In some aspects, the anti-VEGF agent is bevacizumab. In certain aspects, the amount of bevacizumab administered is about 2.5 mg. In other aspects, the anti-VEGF agent is injected at a site of new blood vessel growth in the affected eye. In other aspects, the anti-VEGF agent is administered by injection. In some aspects, the anti-inflammatory steroid is prednisolone acetate. In certain aspects, the anti-inflammatory steroid is prednisolone acetate 1%. In other aspects, the anti-inflammatory steroid is difluprednate. In certain aspects, the anti-inflammatory steroid is difluprednate 0.05%. In some aspects, the anti-inflammatory steroid is triamcinolone acetonide. In certain aspects, the amount of triamcinolone acetonide administered is 40 mg. In still other aspects, the anti-inflammatory steroid is in the form of an ophthalmic solution or suspension. In certain aspects the anti-inflammatory steroid is administered topically. In still other aspects, the anti-inflammatory steroid is injected. In some aspects, the anti-inflammatory steroid is co-injected with the anti-VEGF agent. In other aspects, the NSAID is selected from the group consisting of diclofenac, ketorolac, bromfenac and nepafenac. In certain aspects, the NSAID is in the form of an ophthalmic solution or suspension. In other aspects, the NSAID is selected from the group consisting of diclofenac 0.1%, ketorolac tromethamine ophthalmic solution 0.4%, bromfenac ophthalmic solution 0.09%, and nepafenac ophthalmic suspension 0.1%. In some aspects, the NSAID is administered topically.

In some aspects, the above treatments are performed in conjunction with surgery to remove pterygium. In certain aspects, the treatment is commenced within 2 weeks prior to or following the surgery to remove pterygium. In other aspects, the treatment is commenced within 1 week prior to or following the surgery to remove pterygium. In certain aspects, the treatment is commenced following surgery to remove pterygium. In other aspects, the treatment is commenced within 2 weeks following the surgery to remove pterygium. In other aspects, the treatment is commenced within 1 week following the surgery to remove pterygium. In certain aspects, the commencement of the treatment comprises administering at least one of (1) the anti-VEGF agent; (2) the anti-inflammatory steroid and (3) the non-steroidal anti-inflammatory drug (NSAID). In certain aspects, the treatment comprises more than one administration of the anti-VEGF agent to the affected eye of the subject. In other aspects, the treatment comprises more than one administration of the anti-inflammatory steroid or the NSAID or both to the affected eye of the subject. In certain aspects, the anti-VEGF agent is administered at least once before the anti-inflammatory steroid or the NSAID or both are administered. In other aspects, the anti-inflammatory steroid or the NSAID is administered to the affected eye of the subject at least once before the anti-VEGF agent is administered. In some aspects, the anti-inflammatory steroid and the NSAID are each administered to the affected eye of the subject at least once before the anti-VEGF agent is administered. In other aspects, the anti-VEGF agent, the anti-inflammatory steroid and the NSAID are each administered on separate days at least once. In still other aspects, the anti-VEGF agent and the anti-inflammatory steroid are administered at least once on the same day. In still other aspects, the subject has had pterygium recurrence prior to commencement of the treatment. In certain aspects, the subject is human.

In another aspect, the present disclosure provides a method for treating keloid recurrence, the method comprising administering (1) an anti-VEGF agent to a site where a keloid has been removed from a subject. In certain aspects, the anti-VEGF agent is an antibody or small molecule inhibitor of VEGF signaling. In other aspects, the anti-VEGF agent is an antibody. In some aspects, the anti-VEGF agent is bevacizumab. In certain aspects, the bevacizumab is administered at a dose of 10 mg. In other aspects, the anti-VEGF agent is administered by injection or topically. In certain aspects, the anti-VEGF agent is injected at or adjacent to a site of new blood vessel growth at the site of keloid removal. In some aspects, the treatment further comprises administering to the site (2) an anti-inflammatory steroid or (3) a non-steroidal anti-inflammatory drug (NSAID), or both. In certain aspects, the treatment further comprises administering (1) an anti-VEGF agent, (2) an anti-inflammatory steroid and (3) a non-steroidal anti-inflammatory drug (NSAID) to the site. In certain aspects, the anti-inflammatory steroid is co-administered with the anti-VEGF agent. In other aspects, the anti-inflammatory steroid is applied topically, systemically, or by injection to the site of keloid removal. In certain aspects, the anti-inflammatory steroid is alclometasone, diflorasone, fluocinonide, or prednicarbate. In some aspects, the anti-inflammatory steroid is alclometasone 0.005% cream, diflorasone 0.005% cream, fluocinonide cream 0.1%, or prednicarbate topical 0.1% cream or ointment. In certain aspects, the NSAID is diclofenac. In some aspects, the NSAID is diclofenac 1% solution. In other aspects, the treatment further comprises administering to the site one or more subsequent administrations of the anti-VEGF agent. In some aspects, the treatment further comprises administering to the site one or more subsequent administrations of one or more of an anti-VEGF agent, an anti-inflammatory steroid, and an NSAID. In certain aspects, the subject is human.

Unless otherwise defined, all technical and scientific terms used herein have the same meaning as commonly understood by one of ordinary skill in the art to which this disclosure pertains. In case of conflict, the present document, including definitions provided herein, will control.

All publications, patent applications, patents, GenBank® Accession numbers, protocols and other references mentioned herein are incorporated by reference in their entirety for all purposes. The materials, methods, and examples disclosed herein are illustrative only and not intended to be limiting.

The details of one or more embodiments of the invention are set forth in the accompanying drawings and the description below. Preferred methods and materials are described below, although methods and materials similar or equivalent to those described herein can also be used in the practice or testing of the present invention. Other features, objects, and advantages of the invention will be apparent from the description and drawings, and from the claims.

DETAILED DESCRIPTION

Figure 1:
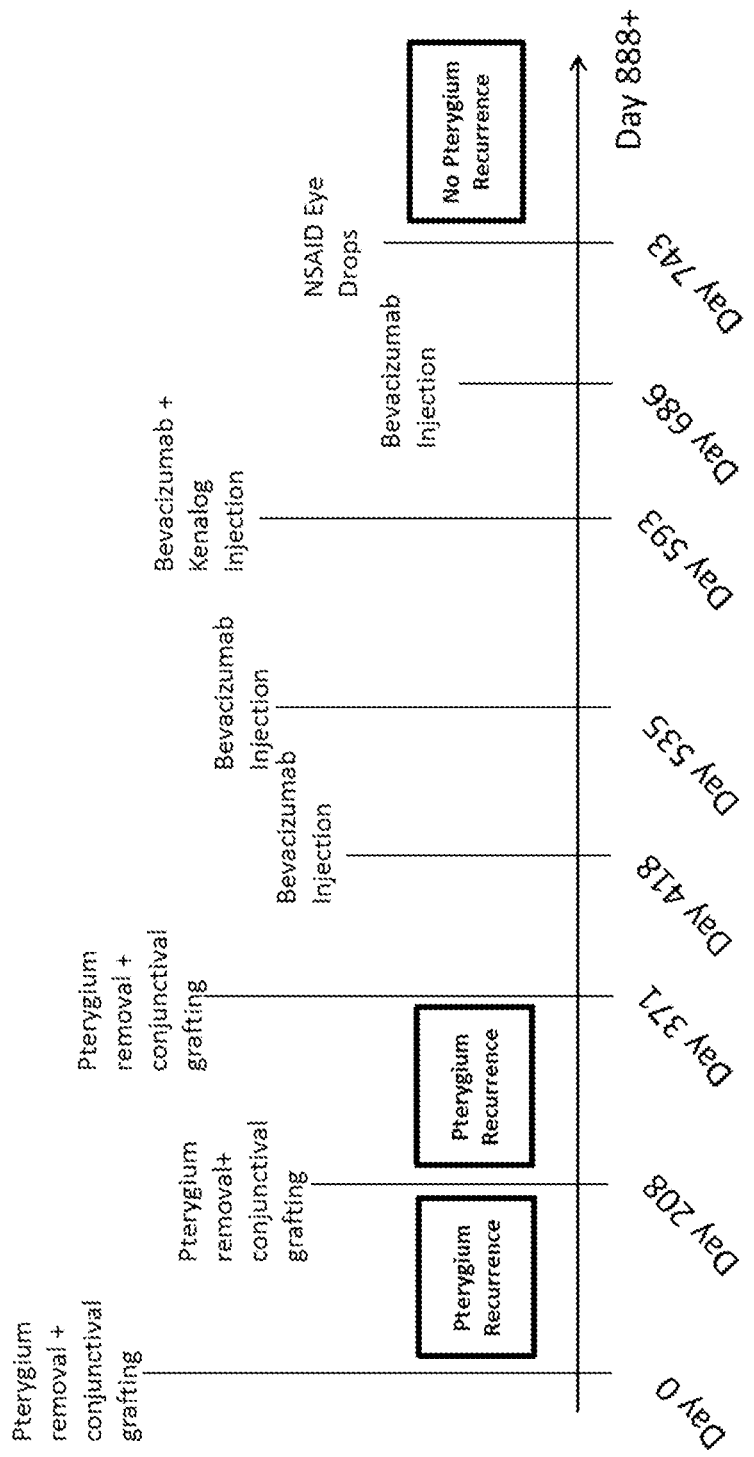
FIGS. 1-5 are timelines showing the treatment regimens of Patients 1-5.

The present disclosure provides methods for treating pterygium recurrence. Pterygia are caused by a neovascular condition of the eye that can eventually lead to blindness. In certain aspects, the methods disclosed herein include administering a combination therapy to an affected eye of a subject with recurrent pterygia. First, a pterygium is removed (e.g., surgically) from an affected eye, and then, following removal, the patient is treated with a combination therapy. The combination therapy disclosed herein includes treating the affected eye with an anti-VEGF agent (such as, e.g., the antibody, bevacizumab, or other inhibitor of VEGF signaling) and with an anti-inflammatory steroid (e.g., triamcinolone acetonide (injected), or prednisolone acetate 1% or difluprednate 0.05% (topical)) and/or a non-steroidal anti-inflammatory drug (NSAID) (e.g., diclofenac 0.1%, ketorolac tromethamine ophthalmic solution, 0.4%, bromfenac ophthalmic solution, 0.09%, nepafenac ophthalmic suspension 0.1%). As disclosed herein, the anti-inflammatory steroid and/or NSAID can be administered before or after the eye is treated with the anti-VEGF agent.

Since it has been reported in the literature that treatment of recurrent pterygia using the anti-VEGF antibody bevacizumab was not effective or only temporarily effective (e.g., 6 months or less), it was surprising to discover, as disclosed herein, that bevacizumab, when administered as part of a combination therapy, was effective for inhibiting pterygium recurrence. For example, as shown in FIGS. 1, 2, 3B, 4, and 5, patients receiving a combination therapy including administration of bevacizumab, steroid and NSAID, have not had recurrence of pterygium in more than 11 months, 8 months, 6 months, 9 months, and 3 months, respectively.

The present disclosure also provides methods for treating keloid recurrence. The methods disclosed herein include administering to the site where a keloid has been removed an anti-VEGF agent, such as, but not limited to an anti-VEGF antibody, e.g., bevacizumab. While not intending to be limited to any one particular theory or mechanism of action, keloids express high levels of VEGF, and thus the administration of anti-VEGF antibody is believed to inhibit neovascularization, which is required for keloid growth. The methods disclosed herein also include administering the anti-VEGF agent in a combination therapy with one or both of an anti-inflammatory steroid (e.g., alclometasone 0.005% cream, diflorasone 0.005% cream, fluocinonide cream 0.1%, or prednicarbate topical 0.1% cream or ointment) and an NSAID (e.g., diclofenac 1% solution).

DEFINITIONS

As used herein, the term "pterygium recurrence" means the reappearance of pterygium in the eye following removal (e.g., surgically) of primary pterygium.

As used herein, the term "subject" means any mammal, and, in particular, a human, and can also be referred to, e.g., as an individual or patient. A "subject in need of treatment" pterygium or keloid recurrence according to the methods disclosed herein is a subject who is at risk of pterygium recurrence or keloid recurrence, e.g., a patient who is about to undergo or has recently (e.g., within about 12, 11, 10, 9, 8, 7, 6, 5, 4, 3, 2 or 1 month(s), about 2 or 1 week(s) or less) undergone, or is about to undergo (e.g., within about 1 month, about 1 week or less) surgery to remove a pterygium or keloid.

As used herein, an "anti-VEGF agent" means an inhibitor of VEGF signaling. Anti-VEGF agents include antibodies (e.g., bevacizumab), antibody fragments (e.g., an antibody light chain (VL), an antibody heavy chain (VH), a single chain antibody (scFv), an F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means), fusion proteins, peptide, nucleic acids (e.g., siRNA, shRNA), and other small molecules, etc. that disrupt the interaction between VEGF (VEGF-A) and its receptor (VEGFR-1/VEGFR-2). Other, non-limiting examples of anti-VEGF agents encompassed by the present disclosure are provided herein below.

As used herein, the term "adjacent to", e.g., in the context of injecting an anti-VEGF adjacent to or near the site of new blood vessel growth, means proximate to (e.g., within about 0.1 mm, 0.2 mm, 0.3 mm, 0.4 mm, 0.5 mm, 1 mm, 2 mm, 3 mm, 4 mm, or 5 mm from the site of blood vessel growth).

As used herein the terms "therapeutically effective" and "effective amount", used interchangeably, applied to a dose or amount refer to a quantity of a composition, compound or pharmaceutical formulation that is sufficient to result in a desired activity upon administration to a subject in need thereof. Within the context of the present invention, the term "therapeutically effective" refers to that quantity of a composition, compound or pharmaceutical formulation that is sufficient to reduce, eliminate or delay at least one symptom of a disease or condition specified herein, e.g., pterygium or keloid recurrence. When a combination of active agents is administered, the effective amount of the combination, or individual agents, may or may not include amounts of each agent that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level.

Therapeutically effective dosages in the methods described herein can be determined by the treating physician. For example, the physician may begin treatment using manufacturer-recommended doses for the anti-VEGF agent, anti-inflammatory steroid and/or NSAID, and make adjustments based on the physician's observations of the effect of treatment. Further guidance is provided herein and in the Examples. In addition, clinical trials can be conducted to determine the doses that are effective to produce statistically significant treatment effects when a population of patients is treated.

As used herein "combination therapy" means the treatment of a subject in need of treatment with a certain composition or drug in which the subject is treated or given one or more other compositions or drugs for the disease in conjunction with the first and/or in conjunction with one or more other therapies, such as, e.g., surgery. Such combination therapy can be sequential therapy wherein the patient is treated first with one treatment modality (e.g., drug or therapy), and then the other (e.g., drug or therapy), and so on, or all drugs and/or therapies can be administered simultaneously. In either case, these drugs and/or therapies are said to be "co-administered." It is to be understood that "co-administered" does not necessarily mean that the drugs and/or therapies are administered in a combined form (i.e., they may be administered separately or together to the same or different sites at the same or different times).

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "treating" or "treatment" of a state, disorder or condition (e.g., pterygium or keloid recurrence) includes: (1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; and/or (2) inhibiting the state, disorder or condition, including arresting, reducing or delaying the development of the disease or a relapse thereof (in case of maintenance treatment) or at least one clinical or sub-clinical symptom thereof; and/or (3) relieving the disease, i.e., causing regression of the state, disorder or condition or at least one of its clinical or sub-clinical symptoms; and/or (4) causing a decrease in the severity of one or more symptoms of the disease. The benefit to a subject to be treated is either statistically significant or at least perceptible to the patient or to the physician.

Treating can include inhibiting pterygium recurrence in a subject. When pterygium recurrence is inhibited, pterygium is not detectable for at least a predetermined time frame in the affected eye of the subject where primary pterygium has been removed. For example, a predetermined time frame may be, e.g., at least 1 month, at least 2 months, at least 3 months, at least 4 months, at least 5 months, at least 6 months, at least 7 months, at least 8 months, at least 9 months, at least 10 months, at least 11 months, or at least 12 months. Preferably, the predetermined time frame is at least 6 months.

Treating can include inhibiting keloid recurrence in a subject. When keloid recurrence is inhibited, keloid is not detectable for at least a predetermined time frame in the site where primary pterygium has been removed. For example, a predetermined time frame may be, e.g., at least 1 month, at least 2 months, at least 3 months, at least 4 months, at least 5 months, at least 6 months, at least 7 months, at least 8 months, at least 9 months, at least 10 months, at least 11 months, or at least 12 months. Preferably, the predetermined time frame is at least 6 months.

Anti-VEGF Agents

The human VEGF-A gene is organized in eight exons. Alternative exon splicing results in the generation of four main VEGF isoforms, having, respectively, 121, 165, 189, and 206 amino acids following signal sequence cleavage (VEGF121, VEGF165, VEGF189, and VEGF206). VEGF165 is believed to be the most physiologically relevant isoform. For a review, see Ferrara et al., *Biochem. Biophys. Res. Commun.*, 2005, 333, 328-335. The amino acid sequences of VEGF-A are well known in the art, and due to splice variation, the sequences are numerous. By way of non-limiting example, the following are exemplary and non-limiting GenBank® Accession Nos. for human VEGF-A ("VEGF") amino acid sequences: AAP86646.1, P15692.2, NP_001191313.1, NP_001165101.1, NP_001165099.1, NP_001165097.1, NP_001165095.1, NP_001020539.2, NP_003367.4, NP_001165093.1, NP_001020541.2, NP_001191314.1, NP_001165100.1, NP_001165098.1, NP_001165096.1, NP_001165094.1, NP_001028928.1, NP_001020540.2, NP_001020538.2, and NP_001020537.2.

There are two VEGF receptor (VEGFR) tyrosine kinases (RTKs), Flt-1, known also as VEGFR-1 and KDR, Flk-1, or VEGFR-2. There is now agreement that VEGFR-2 is the major mediator of the mitogenic, angiogenic, and permeability-enhancing effects of VEGF. For a detailed review of the biological and signaling properties of the VEGFR, see Ferrara, *Endocr. Rev.* 2004, 25, 581-611. The amino acid sequences for the VEGFR are known in the art. By way of non-limiting example, GenBank® accession numbers for VEGFR-1 amino acid sequences include (but are not limited to): NP_001153503.1, NP_002010.2, NP_001153502.1, and NP_001153392.1. The amino acid sequences for the VEGFR-2 are known in the art. By way of non-limiting example, GenBank® accession numbers for VEGFR-2 amino acid sequences include (but are not limited to): NP_002244.1, AAC16450.1, and NP_001153503.1.

Disclosed herein are methods for treating pterygium or keloid recurrence. The methods include administering an anti-VEGF agent to a subject.

The present Examples demonstrate that the anti-VEGF antibody bevacizumab can be used in the present methods. The antibody bevacizumab and its VEGF-binding activity are reviewed in detail in Ferrara et al., *Biochem. Biophys. Res.*

*Commun.*, 2005, 333, 328-335. Bevacizumab may be administered to the eye in an amount of about 2.5 mg. However suitable ranges include, e.g., from about 0.5 mg to about 10 mg, about 1 mg to about 5 mg, about 2 mg to about 4 mg, and about 2 mg to about 3 mg. For example, the antibody can be administered at a dosage in the range of about 0.5 mg/0.1 mL to 10 mg/0.1 mL in a total volume of 0.1 mL. Bevacizumab may be administered to skin (e.g., for the inhibition of keloid recurrence) at a dose about 5-15 mg. In one embodiment, the dose for administration to site of keloid removal (e.g., for inhibition of keloid recurrence) is about 10 mg).

It is to be appreciated, however, that the treatment method described herein can also be performed using other anti-VEGF agents (e.g., VEGF or VEGFR inhibitors, such as, but not limited to, other anti-VEGF antibodies, drugs, prodrugs, small molecules, peptides, nucleic acid inhibitors (e.g., siRNA, shRNA, antisense oligonucleotides), fusion proteins, etc.), either that are known in the art or that will be discovered or engineered in the future, so long as the anti-VEGF agent has the ability to inhibit the action of VEGF (e.g., human VEGF) and/or a VEGFR (e.g., VEGFR-1 and/or VEGFR-2) (e.g., human VEGFR-1 or human VEGFR-2) (i.e., to inhibit VEGF signaling). Assays for determining whether an antibody or other agent interferes with VEGF signaling (either by inhibiting VEGF or a VEGFR or the interaction between VEGF and its receptor), for example, are well known in the art, and can be used to determine whether an anti-VEGF agent interferes with VEGF signaling and is therefore encompassed by the presently disclosed methods. Non-limiting examples of such assays include the VEGF inhibition assays described in Vicari et al., *J. Biol. Chem.*, 2011, 286(15), 13612-25 and Brekken et al. Cancer Res., 2000, 60, 5117-24.

By way of non-limiting example, other anti-VEGF antibodies and inhibitors that are known in the art, and, that can be used in the methods disclosed herein include but are not limited to: ranibizumab, pegaptanib, imatinib, vandetanib, sorafenib, pazopanib, valatanib, vevasiranib, aflibercept, etanercept, anecortave acetate (angiostatic steroid), VEGF-trap (a fusion protein), squalamine lactate, erlotinib, gefitinib (small molecules), Combretastatin A4 Prodrug (an antitubulin/antiangiogenic agent), AdPEDF (Adenovector pigment epithelium-derived factor), Cand5 (siRNA), protein tyrosine kinase 7 inhibitors (PTK7), lipolytic agents, TG100801, AG013958, AL39324, AGN211745 (VEGF receptor blockers), anti-angiogenic VEGF-A(xxx)b family, VEGF Trap (receptor decoy), protein kinase antibodies to tyrosine kinase inhibitor receptors SIM010603, kinase domain receptor antibodies (KDR1.3 and KDR2.6), GS101 aganirsen (an antisense oligonucleotide against insulin receptor substrate aka IRS-1), picropodophyllin (PPP), tetrameric tripeptide, tissue kallikrein, KH906 (a recombinant human VEGF receptor protein fusion), beta-adreno receptor blocker 133-AR, nicotinic acetycholine receptor antagonists, linomide analogue (Lin05), morpholino oligomers (VEGFR1_MOe13), decursin, prorenin, vasohibin and sirolimus. It will be appreciated that because the amino acids sequences (as well as nucleic acid sequences encoding the amino acid sequences) of VEGF and VEGFRs are known in the art, the skilled artisan can readily design additional anti-VEGF agents for use in the presently disclosed methods.

Dosage ranges for anti-VEGF agents, e.g., those disclosed above, can be readily determined by the ordinarily skilled artisan, and can, e.g., first be determined in animal models for determining dosage, safety and efficacy according to standard methods known in the art.

Anti-Inflammatory Steroids

Anti-inflammatory steroids are steroidal compounds that have anti-inflammatory activity and include corticosteroids, including glucocorticoids. Glucocorticoids bind to glucocorticoid receptors in the cytoplasm which may increase the transcription of genes coding for anti-inflammatory proteins, including lipocortin-1, interleukin-10, interleukin-1 receptor antagonist and neutral endopeptidase. Glucocorticoids also inhibit the expression of multiple inflammatory genes, including genes for various cytokines, enzymes, receptors and adhesion molecules. Barnes et al., *Clin. Sci.*, 1998, 94, 557-572.

Suitable anti-inflammatory steroids for injection into the eye and suitable for use in the methods described herein include, e.g., triamcinolone acetonide (Kenalog®, e.g., Kenalog®-40, available from Ranbaxy Laboratories Inc. (0.0147% spray), Triesence® available from Alcon Laboratories Inc., Trivaris® available from Allergan Inc., Trianex® available from Upsher Smith Laboratories Inc.). Suitable dosages of triamcinolone acetonide range from 10 mg/mL to 40 mg/mL with volume given range from 0.5 mL to 1 mL. These steroids can be co-injected with other agents described herein (e.g., with the anti-VEGF antibody). Further injectable anti-inflammatory steroids suitable for use in the methods described herein are listed in Table 1.

TABLE 1

Commercially Available Injectable Steroids

| Steroid | Tradenames |
| --- | --- |
| Methylprednisolone | Depo-Medrol ®; Solu-Medrol ® |
| Dexamethasone | Decadron ® -LA; Decadron ® Phosphate |
| Betamethasone | Celestone ® |
| Hydrocortisone | Various |
| Triamcinolone | Aristocort ®, Kenalog ® |

Suitable steroids for topical administration to the eye (e.g., as eye drops or ointment) include, e.g., prednisolone acetate 1% (e.g., Pred Forte®, Allergan Inc.) or difluprednate 0.05%. Suitable dosages for administration to humans include, e.g., one drop to eye with frequency ranging from every hour to every 24 hours depending on the degree of inflammation characterized by redness, swelling, pain and intraocular pressures. Further commercially available topical ocular steroids suitable for use in the methods described herein are listed in Table 2.

TABLE 2

Commercially Available Topical Ocular Steroids

| Steroid | Tradenames | Concentration/Formulation |
| --- | --- | --- |
| Prednisolone acetate | Pred Forte ® | 1.0% suspension |
| | Econopred ® Plus (Alcon) | 1.0% suspension |
| | AK-Tate ™ | 1.0% suspension |
| | Pred Mild ® | 0.125% suspension |
| | Econopred ® | 0.125% suspension |
| Prednisolone sodium phosphate | Inflamase ® Forte | 1.0% solution |
| | Metreton ™ | 0.5% solution |
| | Inflamase ® Mild | 0.125% solution |
| | AK-Pred ™ | 0.125% solution |
| Dexamethasone alcohol | Maxidex ® | 0.1% suspension ointment |
| | Tobradex ® | 0.1% suspension ointment |
| Fluorometholone acetate | Flarex ® | 0.1% suspension |
| | Eflone ™ | 0.1% suspension |
| Fluorometholone alcohol | FML ® | 0.1% suspension |
| | Fluor-Op ™ | 0.1% ointment |
| | FML ®-Mild | 0.25% suspension |

TABLE 2-continued

Commercially Available Topical Ocular Steroids

| Steroid | Tradenames | Concentration/Formulation |
|---|---|---|
| Rimexolone | Vexol ® | 1% suspension |
| Medrysone alcohol | HMS ® | 1.0% suspension |
| Lotoprednol etabonate | Lotemax ® | 0.5% suspension |
| | Alrex ® | 0.2% suspension |
| | Zylet ® | 0.5% suspension |

Suitable steroids for application to the skin include, e.g., alclometasone 0.05% cream (generic or Aclovate® 0.05% cream available from PharmaDerm Inc.), diflorasone 0.005% cream, prednicarbate 0.1% (generic, or Dermatop 0.1% cream or ointment available from Sanofi-Aventis US LLC), and fluocinonide cream 0.1% (e.g., Vanos®, available from Medicis Inc.). Suitable dosages for administration to humans include, e.g., 0.05% to 0.1%. Further commercially available topical ocular steroids suitable for use in the methods described herein are listed in Table 3.

TABLE 3

Commercially Available Topical Steroids

| Potency | Drug |
|---|---|
| Super-High | Betamethasone dipropionate, augmented |
| | Clobetasol propionate |
| | Fluocinonide |
| | Flurandrenolide |
| | Halobetasol propionate |
| High | Amcinonide |
| | Betamethasone dipropionate |
| | Desoximetasone |
| | Diflorasone diacetate |
| | Fluocinonide |
| | Halocinonide |
| | Triamcinolone |
| Medium-High | Amcinonide |
| | Betamethasone dipropionate |
| | Betamethasone valerate |
| | Desoximetasone |
| | Diflorasone diacetate |
| | Fluocinonide |
| | Fluticasone propionate |
| | Mometasone furoate |
| | Triamcinolone acetonide |
| Medium | Clocortolone pivalate |
| | Fluocinolone acetonide |
| | Hydrocortisone valerate |
| | Mometasone furoate |
| | Triamcinolone acetonide |
| Medium-Low | Betamethasone valerate |
| | Desonide |
| | Fluocinolone acetonide |
| | Fluticasone proprionate |
| | Hydrocortisone butyrate |
| | Hydrocortisone probutate |
| | Hydrocortisone valerate |
| | Prednicarbate |
| | Triamcinolone acetonide |
| Low | Aclometasone dipropionate |
| | Betamethasone valerate |
| | Desonide |
| | Fluocinolone acetonide |
| | Triamcinolone acetonide |
| Very Low | Hydrocortisone (base) |
| | Hydrocortisone acetate/Aloe vera |
| | Hydrocortisone acetate/urea |

Non-Steroidal Anti-Inflammatory Drugs (NSAIDs)

Non-steroidal anti-inflammatory drugs (NSAIDs) are non-steroidal compounds that reduce inflammation. Most NSAIDs act as nonselective inhibitors of the enzyme cyclooxygenase (COX), inhibiting both the cyclooxygenase-1 (COX-1) and cyclooxygenase-2 (COX-2) isoenzymes. COX catalyzes the formation of prostaglandins. Since COX-1 inhibition is believed to be associated with gastrointestinal side-effects of NSAIDs, compounds that are selective COX-2 inhibitors have also been developed.

Non-limiting examples of NSAIDs that can be administered to the eye include, e.g., diclofenac 0.1%, ketorolac tromethamine ophthalmic solution, 0.4% (Allergan Inc.) bromfenac ophthalmic solution, 0.09% (Bausch and Lomb Inc.), nepafenac ophthalmic suspension 0.1% (Alcon Laboratories Inc.) fluriprofen sodium 0.03% solution and ketorolac tromethamine 0.5% solution. Suitable dosage regimens for administration to humans include, e.g., 0.1% applied one drop once a day, up to 4 times a day (every 6 hours).

Non-limiting examples of NSAIDs that can be administered to the skin include, e.g., diclofenac 1% (topical) (e.g., Voltaren gel 1% from Novartis Pharmaceuticals Corp. or Pennsaid 1.5% solution (topical) from Mallinckrodt Pharmaceuticals). Suitable dosages for administration to humans include, e.g., 1% (topical) apply to skin once a day to 40 mg (administer by injecting 1 mL into skin).

Methods of Treating Pterygium and Keloid Recurrence

Provided herein are methods for treating (e.g., inhibiting) pterygium recurrence in an affected eye of a subject, the method including (e.g., comprising, consisting essentially of, consisting of) administering to the affected eye of a subject in need of such treatment (1) at least one anti-VEGF agent (e.g., ranibizumab, pegaptanib, anecortave acetate (angiostatic steroid), VEGF-trap (a fusion protein), squalamine lactate, erlotinib, gefitinib (small molecules), combretastatin A4 prodrug (an antitubulin/antiangiogenic agent), AdPEDF (Adenovector pigment epithelium-derived factor), Cand5 (siRNA), and TG100801 (VEGF receptor blocker); and one or both of (2) an anti-inflammatory steroid (e.g., triamcinolone acetonide, prednisolone acetate 1%, or difluprednate 0.05%.) and (3) a non-steroidal anti-inflammatory drug (NSAID) (e.g., diclofenac 0.1%, ketorolac tromethamine ophthalmic solution 0.4%, bromfenac ophthalmic solution 0.09%, and nepafenac ophthalmic suspension 0.1%).

In a specific embodiment, a method for treating pterygium recurrence in an affected eye of a subject includes (e.g., comprises, consists essentially of, consists of) administering to the affected eye of a subject in need of such treatment (1) bevacizumab and (2) triamcinolone acetonide (or prednisolone acetate 1%, or difluprednate 0.05%.) and/or (3) diclofenac 0.1% (or ketorolac tromethamine ophthalmic solution 0.4%, bromfenac ophthalmic solution 0.09%, or nepafenac ophthalmic suspension 0.1%).

In another specific embodiment, a method for treating pterygium recurrence in an affected eye of a subject includes (e.g., comprises, consists essentially of, consists of) administering to the affected eye of a subject in need of such treatment (1) bevacizumab; and (2) triamcinolone acetonide (or prednisolone acetate 1%, or difluprednate 0.05%).

In another specific embodiment, a method for treating pterygium recurrence in an affected eye of a subject includes (e.g., comprises, consists essentially of, consists of) administering to the affected eye of a subject in need of such treatment (1) bevacizumab; and (2) diclofenac 0.1% (or ketorolac tromethamine ophthalmic solution 0.4%, bromfenac ophthalmic solution 0.09%, or nepafenac ophthalmic suspension 0.1%).

In yet another specific embodiment, a method for treating pterygium recurrence in an affected eye of a subject includes (e.g., comprises, consists essentially of, consists of) administering to the affected eye of a subject in need of such treatment (1) bevacizumab; (2) triamcinolone acetonide (or prednisolone acetate 1%, or difluprednate 0.05%.); and (3) diclofenac 0.1% (or ketorolac tromethamine ophthalmic solution 0.4%, bromfenac ophthalmic solution 0.09%, or nepafenac ophthalmic suspension 0.1%).

Also provided herein are methods for treating (e.g., inhibiting) keloid recurrence, wherein the method includes (e.g., comprises, consists essentially of, or consists of) administering to a site where a keloid has been removed in a subject (1) an anti-VEGF agent (e.g., Ranibizumab, pegaptanib, Anecortave acetate (angiostatic steroid), VEGF-trap (a fusion protein), squalamine lactate, erlotinib, gefitinib (small molecules), combretastatin A4 prodrug (an antitubulin/antiangiogenic agent), AdPEDF (Adenovector pigment epithelium-derived factor), Cand5 (siRNA), and TG100801 (VEGF receptor blocker). In certain aspects, the method further includes administering to the site one or both of (2) an anti-inflammatory steroid (e.g., alclometasone 0.005% cream, diflorasone 0.005% cream, fluocinonide cream 0.1%, or prednicarbate topical 0.1% cream or ointment); and (3) an NSAID (e.g., diclofenac 1% solution).

In a specific embodiment, a method for treating keloid recurrence is provided, wherein the method includes administering (1) bevacizumab. In certain embodiments, the therapy further includes administering to the site (2) alclometasone 0.005% cream, diflorasone 0.005% cream, fluocinonide cream 0.1%, or prednicarbate topical 0.1% cream or ointment. In another embodiment, a method for treating keloid recurrence is provided, wherein the method includes administering to the site (of previous keloid removal) (1) bevacizumab and (2) an NSAID diclofenac solution or gel (e.g., 1% solution or gel). In another embodiment, a method for treating keloid recurrence is provided, wherein the method includes administering to the site (of previous keloid removal) (1) bevacizumab, (2) alclometasone or diflorasone cream (e.g., 0.005% cream), or prednicarbate topical 0.1% cream or ointment; and (3) an NSAID (e.g., diclofenac 1% solution).

When a combination therapy is administered to a subject, it will be appreciated that the agents administered as part of the combination therapy can be administered in any order, e.g., as determined appropriate, e.g., by the subject's physician. For example, a subject may be first administered an anti-inflammatory steroid (e.g., eye drop or skin cream), followed by injection or other suitable route of administration of an anti-VEGF agent (e.g., as disclosed herein), followed by topical administration of an NSAID (e.g., eye drop, ointment, or skin cream). However, in other embodiments, the subject may be first administered an NSAID, followed by injection or other suitable route of administration of an anti-VEGF agent (e.g., as disclosed herein) alone, followed by topical administration of an anti-inflammatory steroid, or followed by injection (e.g., co-injection) or other suitable route(s) of administration of the anti-VEGF agent and an injectable steroid. In another embodiment, the subject can be first administered an anti-VEGF agent, by a suitable route of administration, followed by an NSAID and then an anti-inflammatory steroid, or the subject can be first administered an anti-VEGF agent by a suitable route of administration, followed by an anti-inflammatory steroid, followed by an NSAID. In other embodiments, all two or all three agents (anti-VEGF agent, anti-inflammatory steroid and/or NSAID) can be administered together, e.g., at or near the same time, e.g., within 1, 2, 3, 4, 6, 8, 10, 12 or 24 hours of each other. It is also contemplated that more than one anti-VEGF agent can be administered in combination in the methods disclosed herein (either at the same or different times, by the same or different route(s) of administration).

The length of time between removal of the pterygium or keloid and the first treatment can vary according to each patient's needs. For pterygia, it is typical to wait at least a day or two following the surgery, for example, to inject anti-VEGF antibody, simply to give the patient time to recover. However, it is also possible to inject the anti-VEGF antibody and/or injectable steroid, as well apply topical steroid and/or NSAID on the day of surgery. Treatment, e.g., with a combination therapy disclosed herein can also begin, about 2 or more, about 3 or more, about 4 or more, about 5 or more, about 6 or more, or about 7 or more days after surgery, about 1 or 2 weeks or more, about 3 weeks or more, about 4 weeks or more, or about 5 weeks or more after the surgery. The treatment can also be commenced in preparation for surgery, e.g., by administering one or more of the drugs within about 1 week prior to the surgery.

Time between administrations of the different components (antibody, steroid, and/or NSAID) of the combination therapy can also range widely depending on each patient's needs. When two or more agents of the combination therapy are not administered on the same day, they can be administered about 1 or more, about 2 or more, about 3 or more, about 4 or more, about 5 or more, about 6 or more, or about 7 or more days apart, about 1 or 2 weeks or more, about 3 weeks or more, about 4 weeks or more, or about 5 weeks or more apart.

The methods disclosed herein provide an improved treatment of pterygium and keloid. As discussed above, currently available treatments typically result in recurrence after only a short period of time (e.g., less than about 6 months). The presently disclosed methods provide long-term treatments (including complete inhibition) of pterygium and keloid recurrence (e.g., greater than about 6, 7, 8, 9, 10 or 11 months following removal of the pterygium or keloid). Typically, although not necessarily, treatment with the combination therapy disclosed herein can continue until a patient is determined to have no new blood vessel growth and no pterygium recurrence for about 6 months from the time of the last treatment. At that time, the patient may continue to receive NSAID drug (e.g., NSAID eye drops), which may be administered for up to, e.g., about one year.

Administration

Compositions and formulations including an antibody, steroid and/or NSAID ("agent") as described herein can be administered topically or parenterally, or by any other suitable methods known in the art. The term "parenteral" includes injection or deposition or sustained release via vehicles or devices (e.g., intravenous, subconjunctival, subtenon, episcleral, intrascleral, subscleral, intraperitoneal, epidural, intrathecal, intramuscular, intraluminal, intratracheal, epidermal, intradermal, subdermal or subcutaneous). Moreover, the different agents administered in the combination therapy disclosed herein may be administered by different routes. For example, an antibody or other anti-VEGF agent disclosed herein may be injection into the eye or skin, or applied topically; an anti-inflammatory steroid and/or or NSAID may be administered systemically (e.g., by injection), orally, and/or topically, e.g., to the eye or skin.

While it is possible to use an agent disclosed herein for therapy as is, it may be preferable to administer the agent as a pharmaceutical formulation, e.g., in admixture with a suitable pharmaceutical excipient, diluent, or carrier selected with regard to the intended route of administration and standard pharmaceutical practice. Pharmaceutical formulations include at least one active compound, in association with a pharmaceutically acceptable excipient, diluent, and/or carrier.

Administration of a composition or formulation can be once a day, twice a day, or more often. Frequency may be decreased during a treatment maintenance phase of the treatmeent, e.g., once every second or third day instead of every day or twice a day. The dose and the administration frequency can be adjusted based on the judgment of the treating physician, for example taking into account the clinical signs, pathological signs and clinical and subclinical symptoms of a disease of the conditions treated with the present methods, as well as the patient's clinical history. For example, higher doses or frequency of administration, or a longer duration of treatment may be indicated when a patient is showing symptoms of pterygium or keloid recurrence (e.g., blood vessel growth), or if the patient has a history of previous pterygium or keloid recurrence. Specific examples of dosage and frequency are provided in the Examples.

It will be appreciated that the amount of an agent disclosed herein required for use in treatment will vary with the route of administration, the nature of the condition for which treatment is required, and the age, body weight and condition of the patient, and will be ultimately at the discretion of the attendant physician or veterinarian. Compositions will typically contain an effective amount of the active agent(s), alone or in combination. Preliminary doses can be determined according to animal tests, and the scaling of dosages for human administration can be performed according to art-accepted practices.

Length of treatment, i.e., number of days, will be readily determined by a physician treating the subject; however the number of days of treatment may range from about 1 day to about 365 days. As provided by the present methods, and discussed below, the efficacy of treatment can be monitored during the course of treatment to determine whether the treatment has been successful, or whether additional (or modified) treatment is necessary.

Kits

In certain embodiments, the present disclosure provides kits for treating pterygium or keloid recurrence in a subject. The kits can include an anti-VEGF antibody (e.g., bevacizumab, Ranibizumab, Pegaptanib) or anti-VEGF agent (e.g., Anecortave acetate (angiostatic steroid), VEGF-trap (a fusion protein), Squalamine lactate (small molecule), Combretastatin A4 Prodrug (an antitubulin/antiangiogenic agent), AdPEDF (Adenovector pigment epithelium-derived factor), Cand5 (siRNA), and TG100801 (VEGF receptor blocker)), and one or more of an anti-inflammatory steroid (suitable for application to eye or skin) (e.g., triamcinolone acetonide, prednisolone acetate 1% and/or difluprednate 0.05% (for eye), or alclometasone 0.005% cream, diflorasone 0.005% cream, fluocinonide cream 0.1%, and/or prednicarbate topical 0.1% cream or ointment (for skin), and an NSAID (e.g., diclofenac 1% gel, diclofenac 1.5% solution (topical)). The skilled artisan will appreciate that the dosages of the above anti-inflammatory steroids and NSAIDs may be varied without departing from the nature of the present disclosure, and thus other dosages are also encompassed by the present disclosure. The skilled artisan will know which dosages of the anti-inflammatory steroids and NSAIDs disclosed herein may be safely and effectively administered to a subject according to the standard of care and knowledge in the art, and can include the anti-inflammatory steroids and NSAIDs described herein.

In a specific embodiment, a kit includes bevacizumab; and one or more of prednisolone acetate 1% and difluprednate 0.05% and triamcinolone acetonide. In another specific embodiment, a kit includes bevacizumab and diclofenac 0.1% (and/or ketorolac tromethamine ophthalmic solution 0.4%, bromfenac ophthalmic solution 0.09%, and/or nepafenac ophthalmic suspension 0.1%). In another embodiment, the kit includes bevacizumab; one or more of: prednisolone acetate 1%, difluprednate 0.05%, and triamcinolone acetonide; and diclofenac 0.1%. In certain embodiments, the kit is for treating pterygium. The kit can further optionally include instructions for use. The kit can further optionally include (e.g., comprise, consist essentially of, consist of) syringes or applicators preloaded with the above mentioned agents and/or vials containing one or more of the agents.

In another embodiment, the kit includes bevacizumab; and one or more of alclometasone 0.005% cream, diflorasone 0.005% cream, fluocinonide cream 0.1%, and prednicarbate topical 0.1% cream or ointment. In another embodiment, the kit includes bevacizumab; and diclofenac 1% solution. In another embodiment, the kit include bevacizumab; one or more of alclometasone 0.005% cream, diflorasone 0.005% cream, fluocinonide cream 0.1%, and prednicarbate topical 0.1% cream or ointment; and diclofenac 1% solution. In certain embodiments, the kit is for treating keloid recurrence. The kit can further optionally include instructions for use. The kit can further optionally include syringes or applicators preloaded with the above mentioned agents and/or vials containing one or more of the agents.

The kits, regardless of type, will generally include one or more containers into which the biological agents (e.g., inhibitors) are placed and, preferably, suitably aliquotted. The components of the kits may be packaged either in aqueous media or in lyophilized form.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press Oxford; Freshney (2000) Culture of Animal Cells: A Manual of Basic Technique. 4th ed. Wiley-Liss; among others. The Current Protocols listed above are updated several times every year.

The following examples are meant to illustrate, not limit, the invention.

EXAMPLES

Materials and Methods

Treatment Protocol

A topical anesthetic (proparacaine 0.5% eye drops or Alcaine manufactured by Alcon Laboratories Inc.) was applied to the eye following recent pterygiectomy (from ~5 days to 2 months following surgery). The patients were examined to identify vascular growth on eye conjunctiva. A syringe containing bevacizumab (Avastin®) (Genentech/Roche) at a mixture of 2.5 mg/0.1 mL was injected into the conjunctiva, and the plunger was drawn back to determine if blood was present in the syringe hub. If blood was present (indicating presence of blood vessel), the syringe needle was withdrawn. Bevacizumab was injected into areas adjacent to vascular growth, where blood vessels were dilated and numerous. If bleeding occurred (e.g., in the form of subconjunctival or subcutaneous hematoma), tamponade with Q-tips® was performed until bleeding stopped; then injection was resumed. In some cases, patients were injected with a combination of bevacizumab and Kenalog®) (KENALOG-40 (triamcinolone acetonide), suspension in an amount between 0.1 mL to 1 mL (1 mg to 40 mg).

Either before or after bevacizumab or bevacizumab/Kenalog® injection (time between treatments varied), patients were treated with one or both of anti-inflammatory steroid eye drops and NSAID eye drops. Anti-inflammatory steroid drops (prednisolone acetate 1% (Allergan)) were given for 6 weeks with frequency range from once a day to 4 times a day (every 6 hours) to every hour (24 drops/day). NSAID eye drops (Diclofenac 0.1% (Bausch and Lomb)) drops (1 mg/mL to 100 mg/mL) were given multiple times, 4 times a day every 6 hours for 3 to 6 months.

Patients were followed up to monitor for appearance of new blood vessel growth in the eye. The presence of new vessel growth was an indication for further treatment (e.g., with injection and/or eye drops (steroid and/or NSAID). In some cases, during the first surgery to remove pterygium, the pterygium was only partially removed (e.g., to prevent necrosis). Thus, in some patients, additional surgeries were subsequently performed to remove remaining quadrants of the pterygium.

Treatment of Chronic Pterygium with Bevacizumab with or without Combination Therapy Five patients (Patients 1-5) underwent surgery to remove primary pterygium (pterygiectomy) from the cornea of one or both eyes followed by conjunctival grafting were treated as described below.

1. Patient 1—Right Eye

A 35 year old patient with pterygium of the right eye was treated by surgical removal of the pterygium and conjunctival grafting. The timeline of the patient's treatment is shown in FIG. 1. Following recurrence of the pterygium, a second surgical removal of the pterygium and conjunctival grafting procedure was performed 208 days after performing the first procedure. Following a further recurrence of the pterygium, a third surgical removal of the pterygium and conjunctival grafting procedure was performed 371 days after performing the first procedure.

The following drug treatments were given on the number of days indicated after the third surgical removal and conjunctival grafting procedure:

Day 47: Bevacizumab injection.
Day 164: Bevacizumab injection.
Day 222: Bevacizumab+Kenalog® injection.
Day 315: Bevacizumab injection.
Day 372: NSAID eye drops treatment started.

New blood vessel growth was observed at the time of the bevacizumab injections.

No pterygium regrowth was observed as of about 520 days following performance of the third surgical removal and conjunctival grafting procedure with the drug treatment as described above.

2. Patient 2—Left Eye

Figure 2:
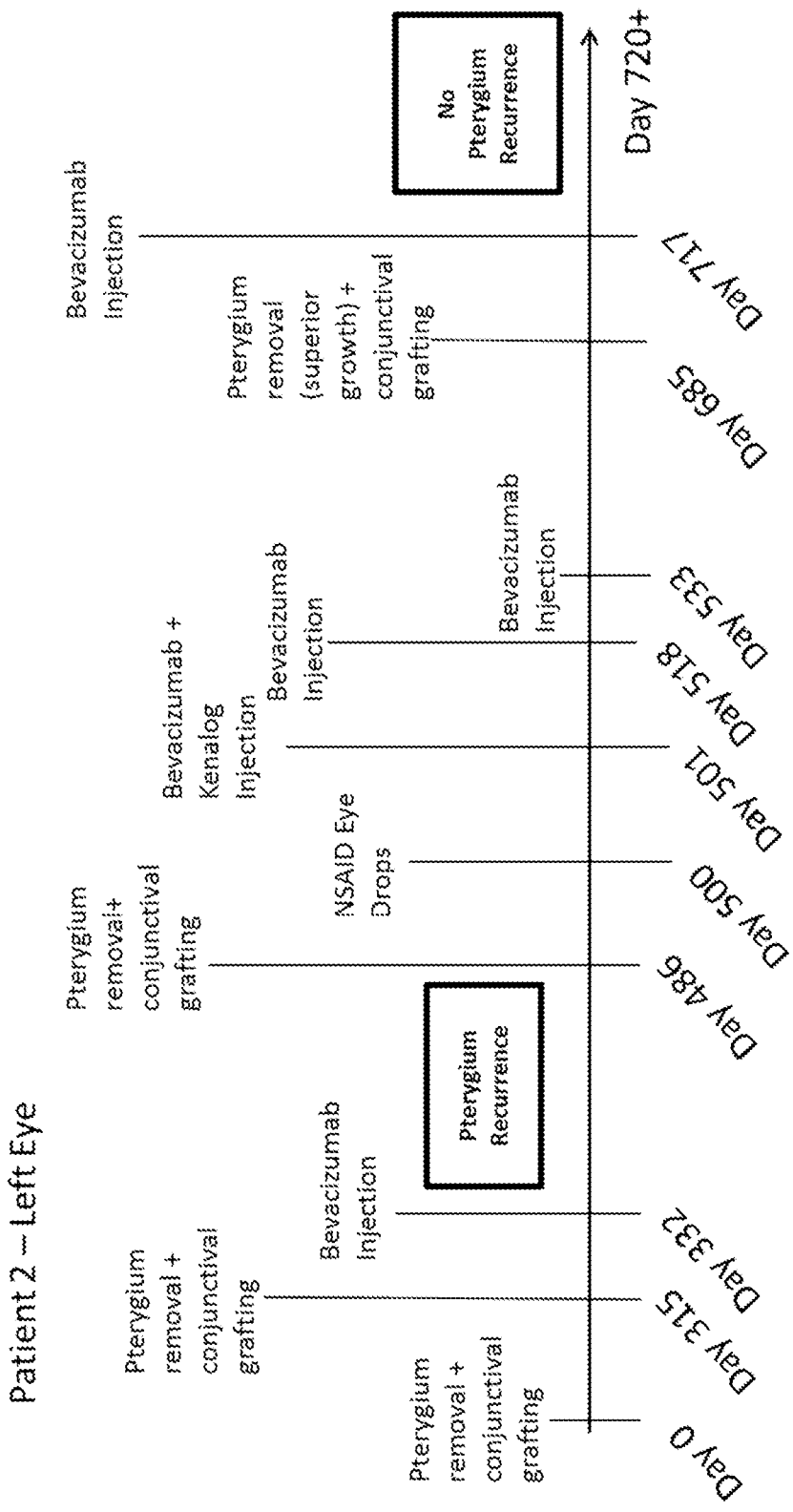

A 58 year old patient presented with pterygium of the left eye. The timeline of the patient's treatment is shown in FIG. 2. The patient was treated by surgical removal of the pterygium and corneal regrafting. Following recurrence of the pterygium, a second surgical removal of the pterygium and conjunctival grafting procedure was performed 315 days after performing the first procedure.

The following drug treatments were given on the number of days indicated after the second surgical removal and conjunctival grafting procedure:

Day 17: Bevacizumab injection.

Following a further recurrence of the pterygium, a third surgical removal of the pterygium and conjunctival grafting procedure was performed 486 days after performing the first procedure.

The following drug treatments were given on the number of days indicated after the third surgical removal and conjunctival grafting procedure:

Day 14: NSAID eye drops treatment started.
Day 15: Bevacizumab and Kenalog® injection.
Day 32: Bevacizumab injection.
Day 47: Bevacizumab and Kenalog® injection.
Day 231: Bevacizumab injection.

In addition, a fourth surgical procedure, superior growth removal, was performed 199 days following the third pterygium removal and surgical grafting procedure. It is noted that superior growth is not pterygium regrowth. The superior growth was a portion of pterygium that was not removed in previous surgeries. Only one quadrant of the pterygium could be removed each time (in each surgery), because removing too many quadrants at once could cause necrosis of the eye.

No pterygium regrowth was observed as of about 240 days following performance of the third surgical removal and conjunctival grafting procedure with the drug treatment described above.

3. Patient 3

A 52 year old patient with pterygium of both the left eyes was treated as described below. A timeline of the patient's treatment is shown in FIGS. 3A and 3B.

Left Eye

Figure 3A:
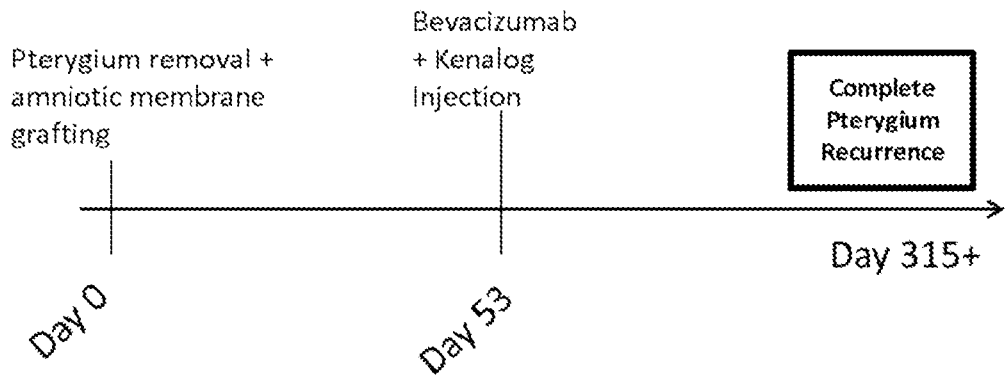
Figure 3B:
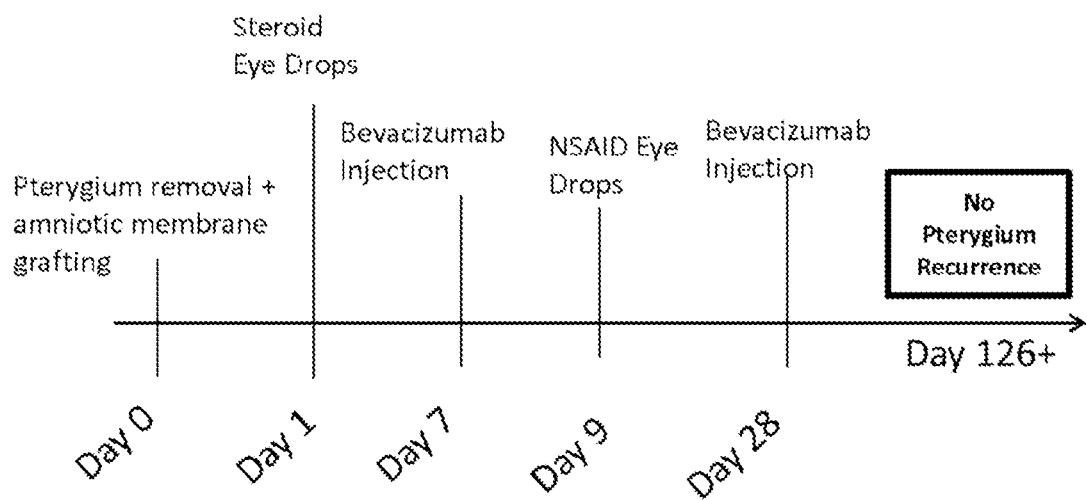

The timeline for the treatment of the patient's left eye is shown in FIG. 3A. The patient's left eye was treated by surgical removal together with grafting of an amniotic membrane manufactured by IOP Ophthalmics on Day 0. The following drug treatments were given on the number of days indicated after the surgery was performed on the left eye:

Day 53: Bevacizumab and Kenalog® injection into left eye.

No NSAID drop was used in the left eye.

Pterygium completely regrew in the patient's left eye.

Right Eye

The timeline for the treatment of the patient's right eye is shown in FIG. 3B. The patient's left eye was treated by surgical removal together with grafting of an amniotic membrane manufactured by IOP Ophthalmics. This procedure was performed 189 days following surgical removal and grafting procedure performed on the left eye. The following drug treatments were given on the number of days indicated after surgery was performed on the right eye:

Day 1 Steroid eye drops treatment started.
Day 8: Bevacizumab injection into right eye.
Day 9: NSAID eye drops treatment started.
Day 28: Bevacizumab injection into right eye.

No regrowth of pterygium into the patient's right eye was observed as of about 130 days following performance of the surgical removal and amniotic membrane grafting procedure on the right eye.

4. Patient 4—Right Eye.

Figure 4:
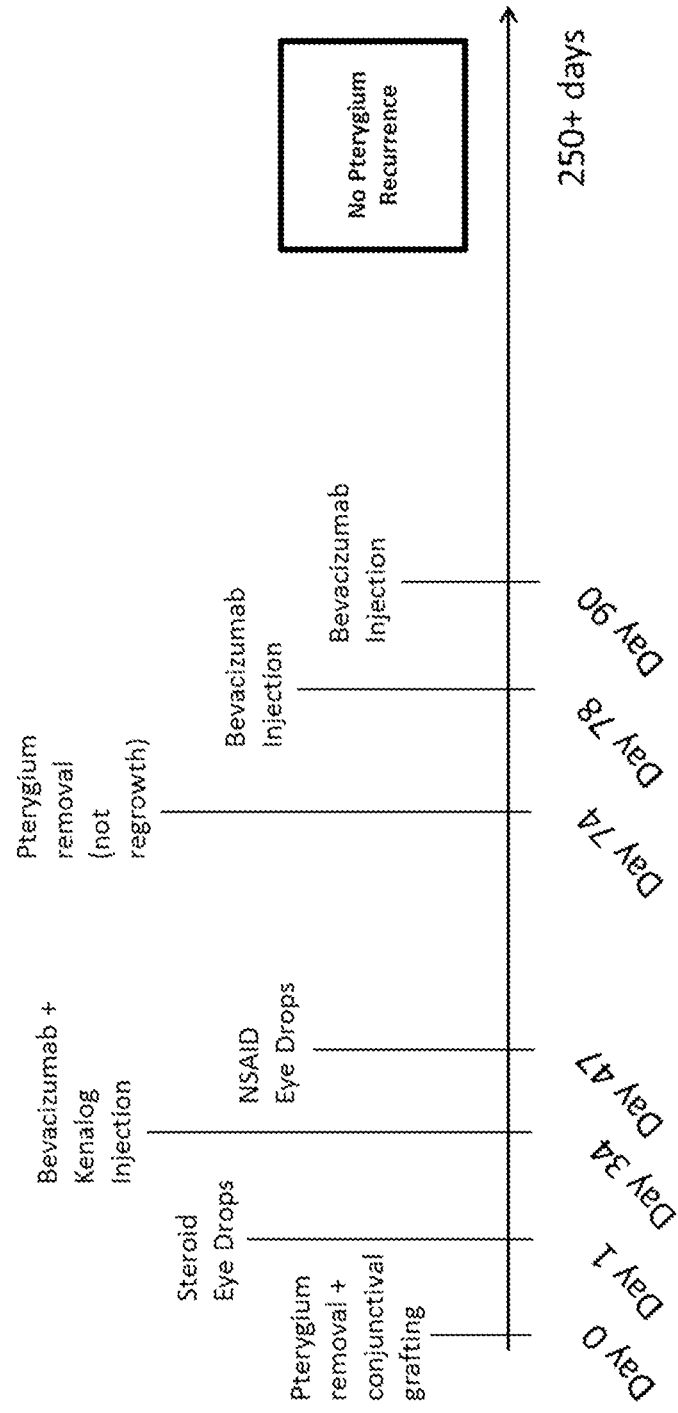

A 70 year old patient presented with pterygium of the right eye. The timeline of the patient's treatment is shown in FIG. 4. The patient was treated on Day 0 by surgical pterygiectomy and conjunctival grafting. The following drug treatments were given on the number of days indicated after surgery was performed on the right eye:

Day 1: Steroid eye drops first used in right eye.
Day 34: Bevacizumab and Kenalog® injections into right eye.
Day 47: NSAID eye drop first used in right eye.
Day 78: Bevacizumab injection into right eye.
Day 90: Bevacizumab injection into right eye.

On day 74 following the initial surgery, a further pterygiectomy procedure was carried out on the patient's right eye to remove pterygium that could not be removed during the first surgery because of scarring.

No regrowth of pterygium into the patient's right eye was observed as of about 250 days following performance of first surgical procedure to remove pterygium from the patient's right eye.

5. Patient 5—Right Eye

Figure 5:
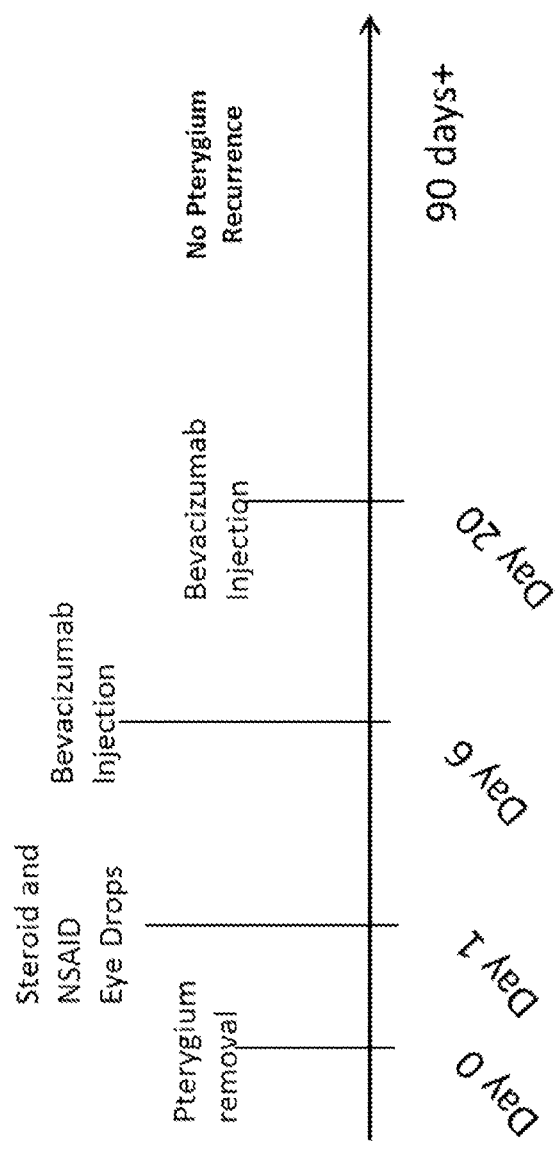

A 66 year old patient presented with pterygium of the right eye. A timeline of the patient's treatment is shown in FIG. 5. The patient was treated by surgical pterygiectomy and amniotic membrane grafting (manufactured by Biotissue). The following drug treatments were given on the number of days indicated after surgery was performed on the patient's right eye:

Day 1: Steroid eye drops and NSAID eye drops treatment started.
Day 34: Bevacizumab and Kenalog® injections into right eye.
Day 6: Bevacizumab injection into right eye.
Day 20: Bevacizumab injection into right eye.

No regrowth of pterygium into the patient's right eye was observed as of about 90 days following performance of surgical procedure to remove pterygium from the patient's right eye.

The various treatment regimens (combination therapies) and results for patients 1-5 are summarized in Table 4, below:

TABLE 4

| Patient | | Bevacizumab Treatment | Steroid (injected and/ or eye drops) | Topical NSAID (eye drops) | Pterygium Recurrence |
|---|---|---|---|---|---|
| 1 | Right eye | Yes | Yes | Yes | No |
| 2 | Left eye | Yes | Yes | Yes | No |
| 3 | Right Eye | Yes | Yes | Yes | No |
|   | Left Eye | Yes | Yes | No | Yes |
| 4 | Right Eye | Yes | Yes | Yes | No |
| 5 | Right Eye | Yes | Yes | Yes | No |

The above results demonstrated that pterygium regrowth was inhibited when the patient received a combination therapy including administration of bevacizumab, an anti-inflammatory steroid (injected or topical), and a topical NSAID, and that the combination therapy was superior to treatment with bevacizumab alone.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating pterygium recurrence comprising administering to an affected eye of a subject in need of such treatment (1) an anti-VEGF agent; and (2) an anti-inflammatory steroid, thereby treating the pterygium recurrence.

2. The method of claim 1, wherein the anti-VEGF agent is an antibody or small molecule inhibitor of VEGF signaling.

3. The method of claim 1, wherein the anti-VEGF agent is the antibody bevacizumab.

4. The method of claim 3, wherein the amount of bevacizumab administered is about 2.5 mg.

5. The method of claim 1, wherein the anti-VEGF agent is injected at a site of new blood vessel growth in the affected eye.

6. The method of claim 1, wherein the anti-inflammatory steroid is one of prednisolone acetate, difluprednate, and triamcinolone acetonide.

7. The method of claim 1, wherein the anti-inflammatory steroid is administered topically.

8. The method of claim 1, wherein the anti-inflammatory steroid is injected into the affected eye.

9. The method of claim 1, wherein the treatment is performed in conjunction with surgery to remove pterygium.

10. The method of claim 1, wherein the treatment comprises more than one administration of one or both of the anti-VEGF agent and the anti-inflammatory steroid to the affected eye of the subject.

11. The method of claim 1, wherein the anti-VEGF agent is administered at least once before the anti-inflammatory steroid is administered.

12. The method of claim 1, wherein the anti-inflammatory steroid is administered to the affected eye of the subject at least once before the anti-VEGF agent is administered.

13. The method of claim 1, wherein the subject has had pterygium recurrence prior to commencement of the treatment.

14. The method of claim 1, comprising administering (1) an anti-VEGF agent, (2) an anti-inflammatory steroid and (3) a non-steroidal anti-inflammatory drug (NSAID) to the affected eye of the subject.

15. The method of claim 14, wherein the NSAID is selected from the group consisting of diclofenac, ketorolac, bromfenac and nepafenac.

16. The method of claim 14, wherein the NSAID is administered topically.

17. The method of claim 14, wherein the anti-VEGF agent is an antibody or small molecule inhibitor of VEGF signaling.

18. The method of claim 14, wherein the anti-VEGF agent is the antibody bevacizumab.

19. The method of claim 18, wherein the amount of bevacizumab administered is about 2.5 mg.

20. The method of claim 14, wherein the anti-VEGF agent is injected at a site of new blood vessel growth in the affected eye.

21. The method of claim 14, wherein the anti-inflammatory steroid is one of prednisolone acetate, difluprednate, and triamcinolone acetonide.

22. The method of claim 14, wherein the anti-inflammatory steroid is administered topically to or is injected into the affected eye.

23. The method of claim 14, wherein the treatment is performed in conjunction with surgery to remove pterygium.

24. The method of claim 14, wherein the treatment comprises more than one administration of one or more of the anti-VEGF agent, the anti-inflammatory steroid, and the NSAID to the affected eye of the subject.

25. The method of claim 14, wherein the anti-VEGF agent is administered at least once before the anti-inflammatory steroid or the NSAID or both are administered.

26. The method of claim 14, wherein the anti-inflammatory steroid or the NSAID is administered to the affected eye of the subject at least once before the anti-VEGF agent is administered to the affected eye of the subject.

27. The method of claim 14, wherein the anti-inflammatory steroid and the NSAID are each administered to the affected eye of the subject at least once before the anti-VEGF agent is administered.

28. The method of claim 14, wherein the subject has had pterygium recurrence prior to commencement of the treatment.

29. A method for treating pterygium recurrence comprising administering to an affected eye of a subject in need of such treatment at least two administrations of the antibody bevacizumab and at least one administration of an anti-inflammatory steroid, wherein the at least two administrations of the bevacizumab occur on separate days.

30. The method of claim 29, wherein the anti-inflammatory steroid is triamcinolone acetonide.

* * * * *